(12) United States Patent
Malinin

(10) Patent No.: US 9,839,524 B2
(45) Date of Patent: Dec. 12, 2017

(54) MODIFIED, PLIABLE, AND COMPRESSIBLE CORTICAL BONE FOR SPINAL FUSIONS AND OTHER SKELETAL TRANSPLANTS

(71) Applicant: Theodore Malinin, Key Biscayne, FL (US)

(72) Inventor: Theodore Malinin, Key Biscayne, FL (US)

( * ) Notice: Subject to any disclaimer, the term of this patent is extended or adjusted under 35 U.S.C. 154(b) by 0 days.

(21) Appl. No.: 14/745,642

(22) Filed: Jun. 22, 2015

(65) Prior Publication Data

US 2016/0367376 A1    Dec. 22, 2016

(51) Int. Cl.
*A61F 2/44* (2006.01)
*A61F 2/30* (2006.01)

(52) U.S. Cl.
CPC ............ *A61F 2/442* (2013.01); *A61F 2/4455* (2013.01); *A61F 2002/3093* (2013.01); *A61F 2002/30622* (2013.01); *A61F 2002/30772* (2013.01); *A61F 2002/444* (2013.01); *A61F 2230/0034* (2013.01); *A61F 2310/00359* (2013.01)

(58) Field of Classification Search
CPC ..... A61F 2/44–2002/4495; A61F 2002/30622; A61F 2230/0034; A61F 2310/00359
See application file for complete search history.

(56) References Cited

U.S. PATENT DOCUMENTS

| | | | | |
|---|---|---|---|---|
| 4,904,261 A | * | 2/1990 | Dove | A61F 2/442 623/17.16 |
| 5,458,638 A | * | 10/1995 | Kuslich | A61F 2/4455 606/247 |
| 5,860,973 A | * | 1/1999 | Michelson | A61B 17/1757 606/247 |
| 6,224,630 B1 | * | 5/2001 | Bao | A61L 31/048 623/16.11 |
| 6,241,771 B1 | * | 6/2001 | Gresser | A61F 2/30965 606/77 |
| 6,245,108 B1 | * | 6/2001 | Biscup | A61F 2/4455 606/246 |
| 6,277,149 B1 | * | 8/2001 | Boyle | A61F 2/4465 623/16.11 |
| 6,530,955 B2 | * | 3/2003 | Boyle | A61F 2/4465 623/17.11 |
| 6,632,247 B2 | * | 10/2003 | Boyer, II | B29C 43/006 623/23.6 |
| 6,660,038 B2 | * | 12/2003 | Boyer, II | B29C 43/006 623/17.15 |
| 6,887,272 B2 | * | 5/2005 | Shinomiya | A61L 27/46 623/16.11 |
| 6,942,698 B1 | * | 9/2005 | Jackson | A61F 2/4455 606/247 |
| 6,986,788 B2 | * | 1/2006 | Paul | A61F 2/28 623/17.11 |
| 7,018,412 B2 | * | 3/2006 | Ferreira | A61F 2/28 606/247 |

(Continued)

*Primary Examiner* — Zade Coley
(74) *Attorney, Agent, or Firm* — Akerman LLP

(57) ABSTRACT

An allogeneic or xenogeneic implant for intervertebral disc replacement includes a body. The body may include one or both of a plurality of grooves or tubular apertures. The body may be formed of partially decalcified bone. The plurality of tubular apertures may be defined within the body and be positioned to allow inflow of decalcifying solutions for rapid and uniform decalcification. After partial decalcification, the body may be pliable and compressible.

29 Claims, 8 Drawing Sheets

(56) References Cited

U.S. PATENT DOCUMENTS

| | | | | |
|---|---|---|---|---|
| 7,077,866 B2* | 7/2006 | Gresser | A61F 2/30965 | 623/17.11 |
| 7,115,146 B2* | 10/2006 | Boyer, II | B29C 43/006 | 623/23.63 |
| 7,335,381 B2* | 2/2008 | Malinin | A61L 27/3608 | 424/549 |
| 7,473,277 B2* | 1/2009 | Boyer, II | B29C 43/006 | 623/17.11 |
| 7,879,103 B2* | 2/2011 | Gertzman | A61F 2/442 | 623/17.16 |
| 8,182,532 B2* | 5/2012 | Anderson | A61F 2/28 | 623/17.11 |
| 8,403,986 B2* | 3/2013 | Michelson | A61B 17/7059 | 623/17.11 |
| 8,608,803 B2* | 12/2013 | Sybert | A61F 2/28 | 623/17.16 |
| 8,709,087 B2* | 4/2014 | Cragg | A61B 17/1671 | 606/80 |
| 2001/0008980 A1* | 7/2001 | Gresser | A61F 2/30965 | 623/17.11 |
| 2001/0034553 A1* | 10/2001 | Michelson | A61F 2/4455 | 623/17.11 |
| 2005/0244457 A1* | 11/2005 | Reddi | A61L 27/3608 | 424/425 |
| 2006/0206208 A1* | 9/2006 | Michelson | A61B 17/7059 | 623/17.11 |
| 2008/0091270 A1* | 4/2008 | Miller | A61F 2/4455 | 623/17.16 |
| 2008/0234822 A1* | 9/2008 | Govil | A61F 2/3094 | 623/17.16 |
| 2009/0018659 A1* | 1/2009 | Malinin | A61F 2/4644 | 623/17.16 |
| 2010/0268339 A1* | 10/2010 | Malinin | A61F 2/447 | 623/17.11 |
| 2011/0009967 A1* | 1/2011 | Malinin | A61F 2/447 | 623/17.11 |
| 2013/0108595 A1* | 5/2013 | Gimble | A61L 27/3608 | 424/93.21 |
| 2013/0209956 A1* | 8/2013 | Sanders | A61C 1/084 | 433/173 |
| 2015/0012107 A1* | 1/2015 | Koford | A61L 27/50 | 623/23.5 |

* cited by examiner

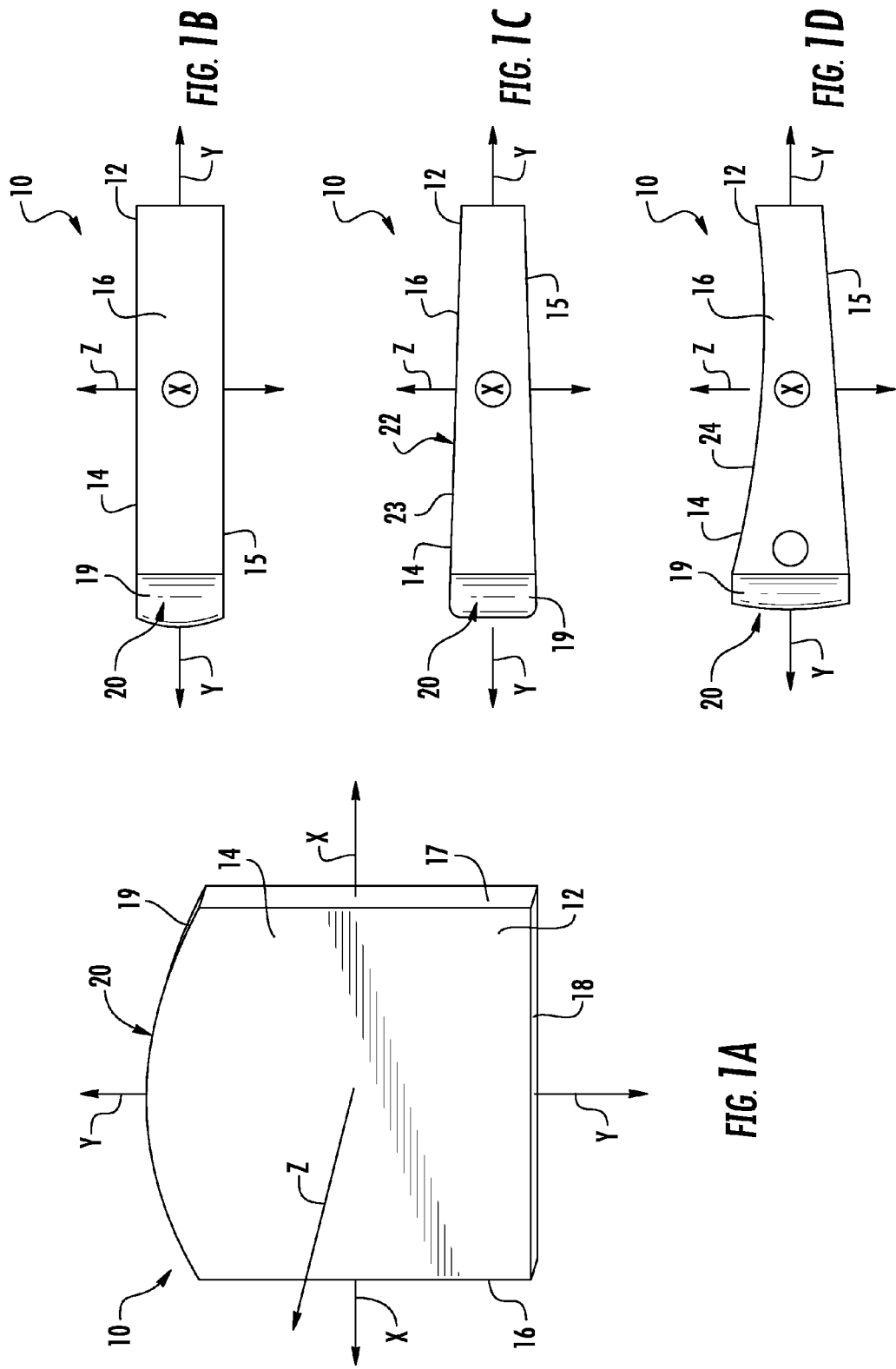

US 9,839,524 B2

MODIFIED, PLIABLE, AND COMPRESSIBLE CORTICAL BONE FOR SPINAL FUSIONS AND OTHER SKELETAL TRANSPLANTS

TECHNICAL FIELD

The present disclosure relates to spinal implants and other bone transplants. More particularly, the present disclosure relates to intervertebral disc implants formed of pliable and compressible cortical bone.

BACKGROUND

In humans and other vertebrate animals the spinal column provides a protective channel to the upper body. The spinal column is made of individual vertebrae that are aligned together and extend along the center of the back. The vertebrae are movably joined at facet joints and are arranged in regions corresponding to the neck, thorax, and lower back. The arrangement within these regions provides the familiar spinal cord and supports the weight and posture of the individual while also enabling a wide range of motion along the curves and arches of the spinal column. To enable bending, twisting, and rotating of the upper body, the individual vertebrae are separated by intervertebral discs. The intervertebral disc are composed of tough fibrous connective tissue that ring around and surround a thick jelly-like material that makes up the disc. The disc acts to dampen shock transmitted along the spinal column and to enable motion. Spine curvature is arranged to accommodate all forces and weight placed on the spinal column. This is altered when vertebral bodies are fused, particularly at several levels, creating a flat back deformity.

Postoperative flat back deformity is caused by surgical intervention with fusion without correction for lordosis. The loss of lumbar lordosis with resulting sagittal imbalance has been recognized and termed flat back syndrome.

Intervertebral discs may become damaged or degenerate over time due to disease or abrupt injury such that it may become medically necessary to surgically remove the damaged or degenerated disc. To maintain the intervertebral spacing between two adjacent vertebrae from which the disc has been removed it has been shown to insert an intervertebral implant, onlay, or inlay grafts over the effected spaces to stabilized the same. The intervertebral implant has traditionally been used to promote bone ingrowth across the disc space and to fuse the adjacent vertebrae into a single structure. Allogeneic derived compact cancellous bone is the preferred implant material to promote bone ingrowth into the implanted graft from the adjacent vertebrae or processes. Compact cancellous bone is not pliable and good quality allogeneic derived compact cancellous bone is in short supply while having size limitations. Current supply of allogeneic compact cancellous bone is insufficient to accommodate a large number of patients in need of spinal fusions.

SUMMARY

In one aspect, an allogeneic or xenogeneic implant for intervertebral disc replacement includes a body and a plurality of tubular apertures. The body may be formed of partially decalcified bone and may extend along a longitudinal axis between a superior face and an inferior face, a lateral axis between a first lateral face and a second lateral face, and an anterior-posterior axis between an anterior face and a posterior face. The plurality of tubular apertures may be defined within the body and be positioned to allow inflow of decalcifying solutions for rapid and uniform decalcification during preparation of the bone. After partial decalcification, the body may be pliable and compressible.

In one arrangement, one or more of the apertures may be filled with a filler material. The filler material may comprise one or more of osteogenic material, chondrogenic material, and nucleus pulposus material. The filler material may further comprise at least one material selected from the group consisting of non-demineralized tissue, demineralized tissue, demineralized bone, cartilage or nucleus pulposus, partially demineralized materials, autolyzed antigen-extracted allogeneic bone, and osteogenic bone factors including bone morphogenetic proteins. In one embodiment, the partially decalcified bone may be prepared from bone material comprising cortical bone. The partially decalcified bone may also be prepared from bone material comprising at least one of cortical bone, cancellous bone, and corticocancellous bone. In another embodiment, the partially decalcified bone may be prepared from at least one bone selected from the group consisting of cancellous bone and corticocancellous bone. The bone material may further be obtained from at least one of a femur, tibia, humerus, ilium, and vertebral body.

In further arrangements, the anterior face may extend at a convex angle between the first and second lateral faces. A longitudinal thickness of the body between the superior face and the inferior face may increase between the posterior face to the anterior face to provide a lordotic configuration of a spine of a patient. In one configuration, the superior face and the inferior face may be inclined with respect to each other anteriorly of the posterior face. In some configurations, the superior face and inferior face extend anteriorly from the posterior face at a combined angle greater than 180°. In another configuration, the superior face and the inferior face extend between the posterior face and anterior face approximately parallel. The body may comprise an anterior-posterior length extending between the anterior face and the posterior face. The anterior-posterior length along the first lateral face and the second lateral face may be between approximately 1 cm and approximately 3 cm. An average anterior-posterior length between the anterior face and the posterior face may be approximately 1.5 cm.

In yet additional arrangements, the body may be dehydratable to obtain a dehydrated form and rehydratable to obtain a hydrated form. The body may increase two-fold from the dehydrated form to the hydrated form. A longitudinal length of the body in the hydrated form taken between the superior face and the inferior face may be between approximately 0.2 cm and approximately 3 cm in the hydrated form and may be reducible by approximately 20% upon reversible compression. An anterior-posterior length of the body taken between the anterior face and the posterior face may be reversibly compressible by approximately 40% to approximately 60% in the hydrated form. A lateral length of the body taken between the first lateral face and the second lateral face may be approximately the same in both the dehydrated form and the hydrated form. The anterior-posterior dimension in the dehydrated form may be approximately 0.5 cm.

The implant may further comprise a plurality of grooves defined along a surface of at least one of the superior face, inferior face, first lateral face, and second lateral face. In one arrangement, the grooves comprise ridges that extend across at least one of the superior face and the inferior face. The grooves may also comprise gull-winged shape grooves that extend across at least one of the superior face and the inferior face. The grooves may also comprise serrations that extend across at least one of the first lateral face and the second lateral face. In one configuration, an average anterior-posterior length of the body may be approximately 1.5 cm to approximately 3.5 cm and the grooves may comprise serrations that extend across the first lateral face and the second lateral face. The apertures may comprise a plurality of first apertures and at least one second aperture extending from the superior face to the inferior face. The second aperture may define a larger cross-section than a cross-section of the first apertures. The first apertures may extend from one or more of (a) the first lateral face to the second lateral face, (b) the anterior face to the posterior face, (c) the superior face to the inferior face, (d) the anterior face to at least one of the first lateral face and the second lateral face, (e) the posterior face to at least one of the first lateral face and the second lateral face, and (f) a wall defining the second aperture to one of the first lateral face, second lateral face, anterior face, and posterior face. The first apertures may extend from the superior face to the inferior face substantially parallel to the longitudinal axis, the first lateral face to the second lateral face substantially parallel to the lateral axis, and substantially parallel to the largest dimension of the body. The first apertures may define cross-sections measuring 2 mm to 1 mm or less or 1 mm or less. In one configuration, the implant may be one of frozen, cryopreserved, freeze-dried, hypothermically dehydrated, and chemically dehydrated.

In another aspect, an intervertebral implant comprises a body and a plurality of grooves comprising gull-wing patterned grooves or ridges. The body may be formed of bone and extend along a longitudinal axis between a superior face and an inferior face, a lateral axis between a first lateral face and a second lateral face, and an anterior-posterior axis between an anterior face and a posterior face. The plurality of grooves may be defined in at least one of the superior face and the inferior face. The implant may further includes an osteogenic material received within at least of the plurality of grooves.

The bone may be at least partially decalcified. The bone may be prepared from bone material comprising at least one of cortical bone, cancellous bone, and corticocancellous bone. The bone material may be obtained from at least one of a femur, tibia, humerus, ilium, and vertebral body. In one configuration, the osteogenic potential of the bone may be abolished by hydrogen peroxide treatment. In another configuration, the osteogenic potential of the bone may be abolished by ionizing radiation treatment in doses ranging from approximately 20 Gray to approximately 60 Gray.

The first lateral face, second lateral face, anterior face, and posterior face may together define a general "D" shape. The first lateral face and second lateral face may extend generally straight with respect to the anterior-posterior axis and generally in parallel. The posterior face may extend generally straight with respect to the lateral axis. The anterior face may generally curve away from the posterior face between the first lateral face and second lateral face.

The implant may further comprise a plurality of apertures defined within the body. A microparticulate material may be received in one or more of the plurality of grooves or apertures. The microparticulate material may comprise one or more of microparticulate nucleus pulposus, microparticulate cartilage comprising cartilage obtained from vertebrae end-plates, and microparticulate bone preparations comprising bone from periosteum and endosteum. Bone marrow or cells derived from bone marrow may be positioned in one or more of the plurality of grooves or apertures.

In yet another aspect, an allogeneic or xenogeneic implant for vertical or horizontal mandibular or maxillary ridge augmentation comprises a body formed of partially decalcified bone. The body may extend along a longitudinal axis between a superior face and an inferior face, a lateral axis between a first lateral face and a second lateral face, and an anterior-posterior axis between an anterior face and a posterior face. The posterior face, first lateral face, anterior face, and second lateral face may together define an arcuate cross-section of the body such that the body comprises a cylindrical shape. A plurality of tubular apertures may be defined within the body. The apertures may be positioned to allow inflow of decalcifying solutions for rapid and uniform decalcification, wherein, after partial decalcification, the body is pliable and compressible.

BRIEF DESCRIPTION OF THE DRAWINGS

The novel features of the described embodiments are set forth with particularity in the appended claims. The described embodiments, however, both as to organization and manner of operation, may be best understood by reference to the following description, taken in conjunction with the accompanying drawings in which:

FIGS. 1A-1D illustrate body plans for implants according to various embodiments described herein;

DESCRIPTION

Figure 2A:
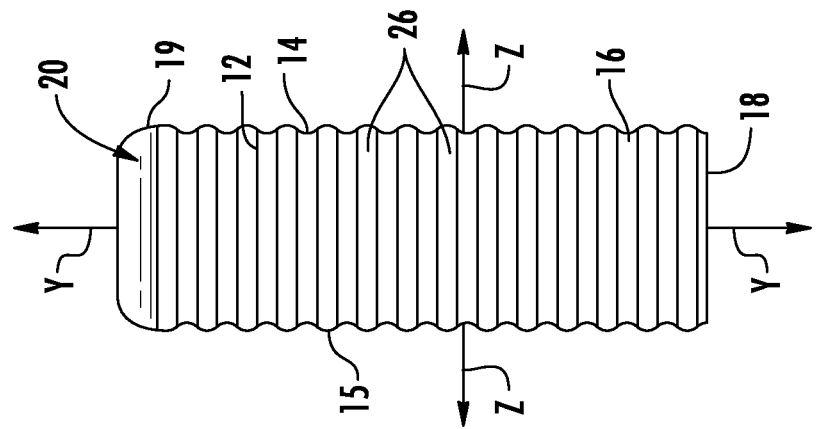
FIGS. 2A-2C illustrate grooves formed in surfaces of implant bodies according to various embodiments described herein.

The present disclosure describes bone derived constructs configured for implantation. The constructs may therefore be referred to as implants, which may comprise spinal or intervertebral implants or inlay, onlay, or other graft, and which may also be referred to as a graft herein, suitable for spinal implantation or similar procedures such as intervertebral disc replacement in humans or in some instances other vertebrate animals and thus may also be referred to as an intervertebral disc implant or graft. Bone grafts for use in intervertebral implantation procedures directed to stabilization of the spinal column may be made from allogeneic or xenogeneic derived bone. Such bone grafts may be placed either in an interbody, posterior, or posterolateral position.

The present disclosure will be described with respect to the drawings provided in FIGS. 1A-6C wherein like features are identified by like numerals. However, it is to be understood that the description and accompanying drawings are offered by way of illustration and not as limitation. Thus, while the implants and the accompanying methods of making and using the implants have been described and illustrated in connection with certain embodiments, many variations and modifications will become evident to those skilled in the art upon consideration of the present disclosure and may be made without departing from the spirit and scope of the disclosure. The disclosure is thus not to be limited to the precise details of methodology or construction set forth herein as such variations and modification are intended to be included within the scope of the disclosure.

Referring to FIGS. 1A-6C, an implant 10 according to the embodiments described herein includes a body 12. The body 12 may be formed of or comprise allogeneic or xenogenic bone materials obtained from the bone of a tissue donor. The harvested bone tissues may be obtained from one or more of femur, tibia, humerus, ilium, vertebral bodies, or other bones of the tissue donor. In one embodiment, the implant 10 comprises bone tissue prepared from cortical bone. In another embodiment, the implant 10 comprises bone tissue prepared from corticocanellous bone. In one embodiment, the implant 10 comprises bone tissue prepared from cancellous bone or corticocancellous bone.

The material, size, and shape of the implant 10 may be selected for one or more of ease of implantation, maintenance of proper spinal curvature, and to provide biomechanical strength to support the spinal column where needed. In certain preferred embodiments, the implants 10 described herein may be dimensioned to heal in a manner providing natural positioning of the spine into which it is implanted.

FIGS. 1A-1D illustrate implant body plans according to various embodiments. The body 12 may extend along a longitudinal axis Z between a superior face 14 and an inferior face 15, a lateral axis X between a first lateral face 16 and a second lateral face 17, and an anterior-posterior axis Y between a posterior face 18, and an anterior face 19. The first lateral face 16, second lateral face 17, posterior face 18, and anterior face 19 may together define a general "D" shape. For example, the first lateral face 16 and the second lateral face 17 may extend generally straight or parallel to the anterior-posterior axis Y. However, other body plans may be used to suit a particular procedure. For example, in one embodiment, a lateral to lateral length of the body, e.g., the length of the body 12 along the lateral axis X between the first lateral face 16 and the second lateral face 17 may decrease or increase anteriorly from the posterior face 18 to the anterior face 19. In a further embodiment, one or both of the first lateral face 16 and the second lateral face 17 may extend anteriorly from the posterior face 18 to the anterior face 19 at an angle directed outwardly of the body 12 or inwardly toward the body 12 or the opposing lateral face 16, 17.

In the illustrated embodiment of FIG. 1A, the posterior face 18 extends generally straight with respect to the lateral axis X and connects with the first lateral face 16 and second lateral face 17 along vertices forming approximately right angles. The anterior face 19 connects to the first lateral face 16 and second lateral face 17 at vertices forming angles greater than 90°, which in some embodiments may form arcuate vertices. The anterior face 19 may comprise a convex curved portion 20 or bulge that generally curves outwardly of the body 12 or away from the posterior face 18 between the first lateral face 16 and second lateral face 17. As shown, the convex curved portion of the anterior face 19 extends outwardly of the body 12 and posterior face 18 along an arcuate curve between the first lateral face 16 and the second lateral face 17.

The superior face 14 and the inferior face 15 may extend along generally flat, e.g., a substantially straight line or angle, or may extend along a curved angle between the anterior face 19 and the posterior face 18. FIGS. 1B-1D illustrate various body plans shown along the first lateral face 16. In the embodiment illustrated in FIG. 1B, the superior face 14 and inferior face 15 extend between the anterior face 19 and the posterior face 18 substantially in parallel to each other or the anterior-posterior axis Y. In this embodiment, a longitudinal length of the body 12 along the longitudinal axis Z between the superior face 14 and inferior face 15 remains approximately the same anterior to posterior.

The implant 10 may also include a body plan wherein the superior face 14 and inferior face 15 are positioned to promote lordosis. As shown in FIGS. 1C & 1D, a longitudinal length of the body 12 along the longitudinal axis Z between the superior face 14 and the inferior face 15 increases anteriorly. One or both of the superior face 14 and inferior face 15 may be positioned at an inclined or declined angle 22, e.g., to extend along a generally flat slope 23 (as shown in FIG. 1C) or along a curved slope 24 (as shown in FIG. 1D), between the anterior face 19 and posterior face 18. The slope 23, 24 may preferably be approximately 10° to approximately 15°, however, less slope could be used or greater slope could be used in certain embodiments. In one embodiment, the superior face 14 and the inferior face 15 are positioned in a wedge shape. For example, the superior face 14 and the inferior face 15 may be anteriorly inclined with respect to each other posterior to anterior. In various embodiments, one or both of the superior face 14 and the inferior face 15 may form angles greater than 90° along their respective vertices with the posterior face 18. The body plan of the embodiment of FIG. 1C includes a superior face 14 and inferior face 15 that extend from the posterior face 18 at a combined angle greater than 180°. The superior face 14 forms an angle with the posterior face 18 greater 90° and the inferior face 15 forms an angle with the posterior face 18 approximately 90°. In one embodiment, one of the superior face 14 and the inferior face 15 forms an angle with the posterior face 18 greater 90° and the other of the superior face 14 and the inferior face 15 forms an angle with the posterior face 18 less than 90°, wherein the combined angles of the superior face 14 and inferior face 15 with the posterior face 18 is greater than 180°.

Those having skill in the art will appreciate upon reading the present disclosure that many configurations may be used to increase longitudinal length anteriorly between the posterior face 18 and anterior face 19. For example, the inclined or declined angle 22 may extend only along a portion of the anterior to posterior length of the body 12. Thus, the combined angle of the superior face 14 and inferior face 15 with respect to the posterior face 18 may be less than or approximately 180°, wherein one of the superior face 14 and inferior face 15 includes an inclined or declined angle 22 that is inclined anteriorly of the posterior face 18, beyond the vertex edge. Therefore, the inclined or declined angle 22 may be across the entire anterior to posterior length of the superior face 14 or inferior face 15 or may be along a portion thereof, as depicted in the example shown in FIG. 1D. As described below, the above generally flat slope 23 or curved slope 24 of the superior face 14 or inferior face 15 may further include surface features such as grooves 26 defined along the generally flat slope 23 or curved slope 24.

Figure 2B:
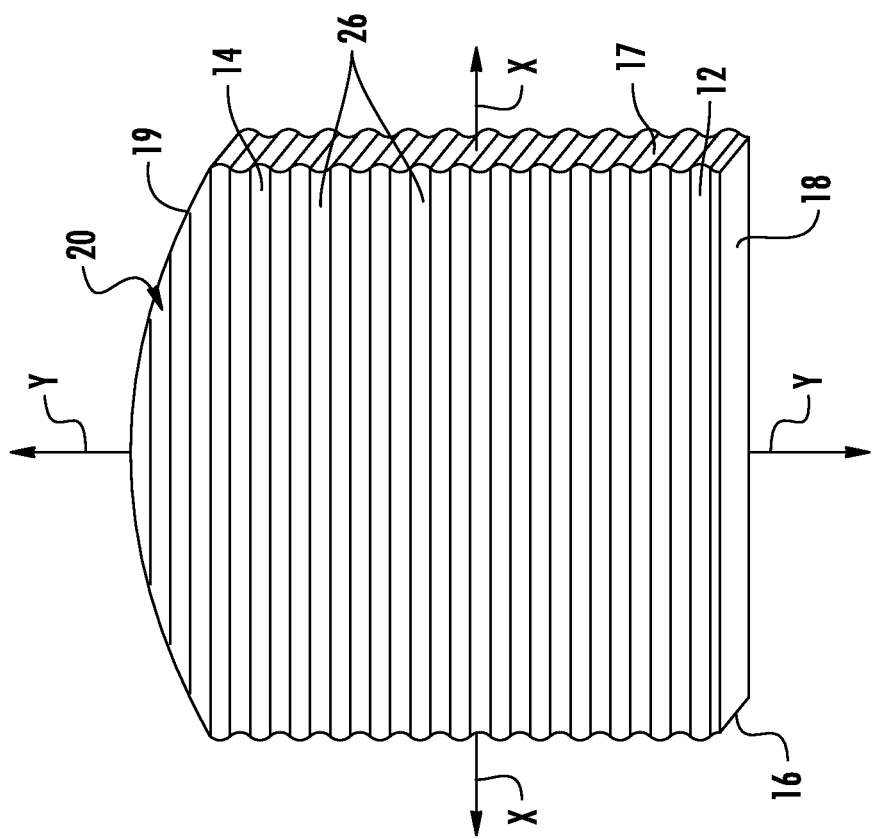
Figure 2C:
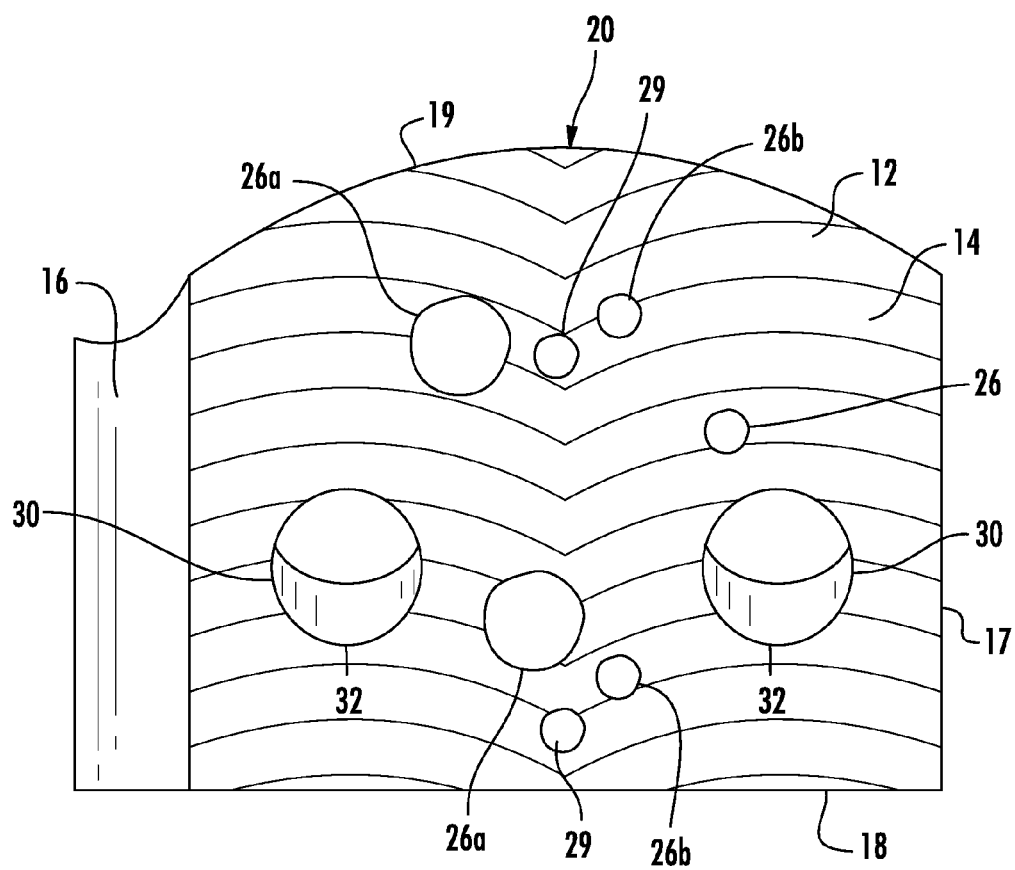

In various embodiments, one or more surfaces of the body 12 may also include one or more grooves 26 defined therein. FIGS. 2A-2C illustrate implants 10 comprising grooves 26 defined along a face surface. While the grooves 26 are shown covering the entirety of the respective faces, in various embodiments, fewer grooves 26 may be used. The implant 10 may be prepared by scoring the bone to provide the one or more grooves 26. The grooves 26 may be configured to prevent slippage, engage vertebra features or processes, provide regions of localized resilience or ingrowth, or to receive filler materials. In some embodiments, a plurality of grooves 26 are defined along a surface of at least one of the superior face 14, the inferior face 15, the first lateral face 16, and the second lateral face 17. In these or other embodiments, a plurality of grooves 26 may be defined on the anterior face 19, the posterior face 18, or both. The grooves 26 may be defined by smooth or course surfaces. The grooves 26 may define arcuate or angled roots. Such grooves 26 may further define arcuate or angled walls extending from the roots to arcuate or angled ridges. Thus, in one embodiment, grooves 26 may comprise one or more ribs or ridges extending from the surface of a face. The grooves 26 may extend partially or entirely across face surfaces. Grooves 26 may also extend along approximately straight paths (see, e.g., FIGS. 2A & 2B) or curved paths (see, e.g., FIGS. 2C, 5A, & 6A). For example, grooves 26 may extend along straight paths parallel to one of the anterior-posterior axis Y, the lateral axis X, and the longitudinal axis Z. Grooves 26 may also extend at angles, such as diagonal to one of the anterior-posterior axis Y, lateral axis X, and longitudinal axis Z. FIG. 2A illustrates grooves 26 that extend along the lateral to lateral length of the body 12, substantially parallel to the lateral axis X or substantially perpendicular to the anterior-posterior axis Y, of at least one of the superior face 14 and the inferior face 15. In this or another embodiment, the grooves 26 may comprise ridges that extend across at least one of the superior face 14 and the inferior face 15.

The grooves 26 may further comprise serrations as shown in FIG. 2B. Grooves comprising serrations or serrated ridges, e.g., along the lateral faces 14, 16 as shown in FIG. 2B, may be dimensioned to promote vascular ingrowth into the body 12 of the graft. Serrations are exemplified along the first lateral face 16 extending substantially parallel to the longitudinal axis Z or substantially perpendicular to the anterior-posterior axis Y. However, in some embodiments, grooves 26 comprising serrations may extend across one or more other faces of the body 12 such as the second lateral face 17, superior face 14, or inferior face 18, instead of or in addition to one or both of the first lateral face 16 and the second lateral face 17. Grooves 26 may be provided in a geometry wherein the roots and associated ridges of the grooves extend in a pattern configured to prevent slippage of the body 12. In one embodiment, for example, as shown in FIG. 2C, grooves 26 extend across a face in a gull-wing pattern. The gull-wing groove pattern comprises curved grooves 26 orientated to prevent slippage of the body 12 after its insertion. In some embodiments, gull-wing patterned grooves 26 may extend across one or more other faces of the body 12, such as the first lateral side 16 or second lateral side 17, instead of or in addition to one or both of the superior face 14 and the inferior face 15. FIG. 2C is a photographic depiction of a spinal graft body 12 having gull-wing patterned grooves 26 defined in its surface. The gull-wing configuration comprises curved grooves 26 that curve to meet at an intersection 29. In the photograph, the grooves 26 are shown to curve and join or intersect at a center portion of the face 14 to form an angle along intersection 29. In FIG. 2C, the grooves 26 intersection at an intersection 29 forming acute angles along a posterior portion of the superior face 14. The intersection 29 forms an angle that increases anteriorly to form an obtuse angle along the an anterior portion of the superior face 14. However, in some embodiments, the intersection 29 forms all acute, right, obtuse, or combinations of such angles thereof.

When grooves 26 extend along multiple faces of the body 12, the grooves 26 may be orientated to be continuous or aligned across two or more faces. For example, grooves 26 may extend along the superior face 14 or the inferior face 15 and the first lateral face 16 or the second lateral face 17 substantially parallel to the anterior-posterior axis Y. In another embodiment, grooves 26 may extend along the superior face 14 or the inferior face 15 and the first lateral face 16 or the second lateral face 17 substantially perpendicular to the anterior-posterior axis Y. In some embodiments, grooves 26 extending along multiple faces of the body may not be aligned or continuous but rather be positioned at non-parallel angles with respect to each other.

Grooves may also extend along one or more of the first lateral face 16, the second lateral face 17, superior face 14, inferior face 15, the posterior face 18, and the anterior face 19 at angles diagonal or at other non-parallel or non-perpendicular angles with respect to a body axis X, Y, Z. In these or other embodiments, grooves may extend along one or more of the first lateral face 16, the second lateral face 17, the superior face 14, the inferior face 15, the posterior face 18, and the anterior face 19 along curved paths. Grooves 26 may also be oriented to be discontinuous or unaligned across as single face or between multiple faces, including adjacent faces.

In another embodiment, an implant 10 comprises a demineralized cortical bone having a flat body 12. A surface of at least one face may include a plurality of grooves 26. The grooves may include any suitable shape or pattern as described above. For example, at least one, such as one or both, of the superior face 16 and the inferior face 17 may include a plurality of gull-wing patterned grooves 26 defined on a surface thereof. Referring again to FIG. 2C, gull-wing patterned grooves 26 may comprise first and second intersecting grooves 26a, 26b. In various embodiments, one or both of the first and second intersecting grooves 26a, 26b may be straight or curved. In one embodiment, the first and second intersecting grooves 26a, 26b each extend along either a straight or curved path. In another embodiment, the first and second intersecting grooves 26a, 26b each extend along curved paths. Various arrangements of first and second intersecting grooves 26a, 26b may be used. For example, in one embodiment, the first and second intersecting grooves 26a, 26b may be arranged in a zig-zag pattern across a face of the body 12. The first and second intersecting grooves 26a, 26b may be arranged in a stacked alignment forming a series of chevrons or curved gull-wings along the one or more faces of the body 12. Areas of intersection 29 between first and second intersecting curves may be located at various, including multiple, positions along a face of the body 12. In one embodiment, the areas of intersection 29 may be aligned or stacked forming an aligned or stacked series of intersections 29 across the face. The areas of intersection 29 may form straight or curved angles along the roots or ridges of the grooves 26. The first and second grooves 26a, 26b may intersect at areas of intersection 29 oriented in one or multiple directions. As shown in FIG. 2C, the first and second grooves 26a, 26b curve toward each other to intersect at intersections 29 forming posteriorly directed angled points or arrowheads. The grooves 26a, 26b intersect at an intersection 29 forming acute angles along a posterior portion of the superior face 14. The grooves 26a, 26b intersection at areas of intersection 29 forming an angle that increases anteriorly to form an obtuse angle along the an anterior portion of the superior face 14. However, in some embodiments, the areas of intersection 29 forms all acute, right, obtuse, or combinations of such angles thereof.

In one embodiment, the first intersecting groove 26a may intersect with the second intersecting groove 26b at approximately mid-way along a face of the body, such as mid-way between the first lateral face 16 and second lateral face 17, superior face 14 and inferior face 15, posterior face 18 and inferior face 17. The first and second intersecting grooves 26a, 26b may each extend along a curved path prior to intersecting. As shown in FIG. 2C, the first and second intersecting grooves 26a, 26b intersect at area of intersection 29 positioned approximately mid-way between the first lateral face 16 and second lateral face 17 along the superior face 14. The intersections 29 are also aligned and stacked along the superior face 14 between the posterior face 18 and anterior face 19. One advantage of disposing the gull-wing patterned grooves across the superior face 14 or inferior face 15 of the body 12 is that grooves 26 may be positioned to provide traction where the surfaces meet the vertebral bone, or any other bone to which the implant is applied, preventing the slippage motion of the body 12.

Figure 3A:
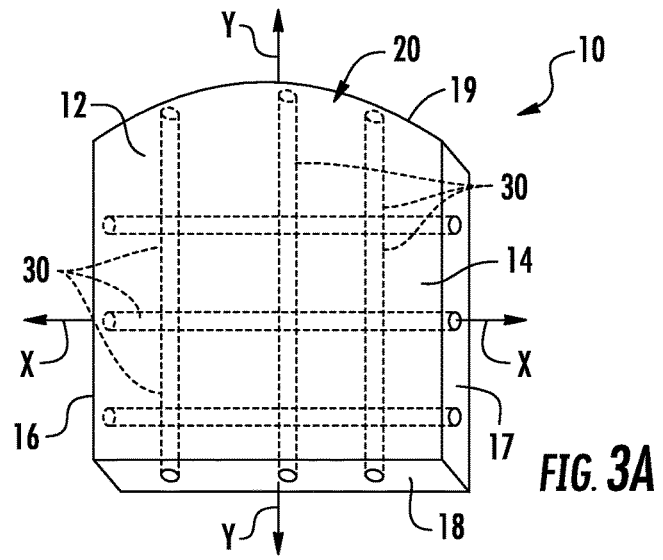
FIGS. 3A-3C illustrate apertures formed within implant bodies according to various embodiments described herein.
Figure 3B:
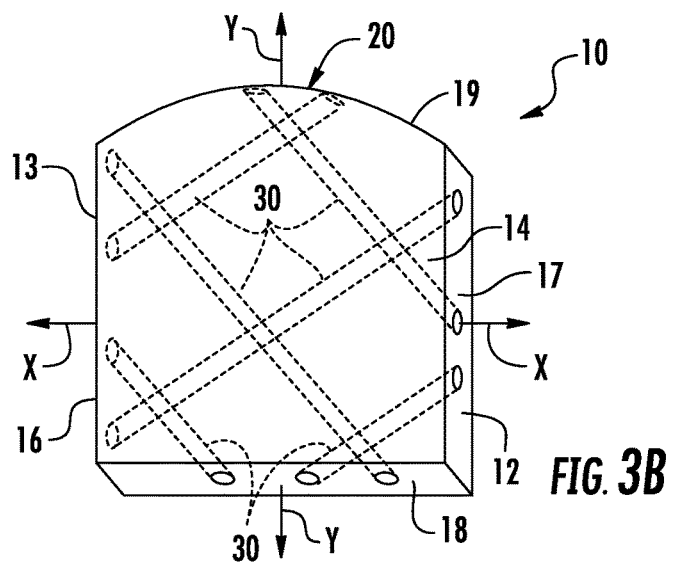
Figure 3C:
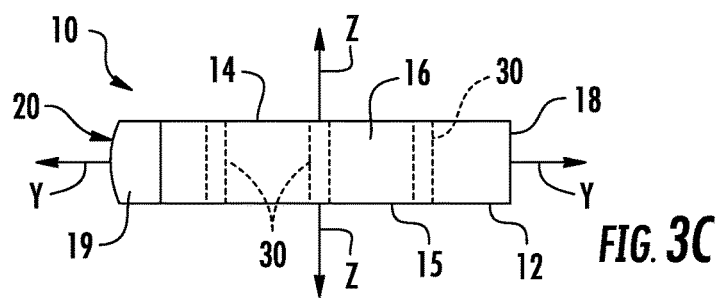

In various embodiments, the implant 10 includes one or more apertures 30 extending within the implant 10. FIGS. 3A-3C illustrate example paths apertures 30 may extend within the body 12. The apertures 30 may be configured to provide biomechanical properties or pathways into or through the implant 10. Apertures 30 may be punched or drilled into the bone during preparation of the implant 10. Apertures 30 may define cross-sections having any desired size or tubular shape, e.g., cubical, cylindrical, spherical, arcuate, or other regular or irregular geometric shape. The size of the apertures 30 may be configured to allow access of decalcifying fluid to adjacent regions of the bone, provide sites for attachment or fixation, or provide a reservoir for filling material, as described in more detail below, or any combination thereof. One or more apertures 30 may extend completely through the body 12, as shown in the illustrated embodiments, or may extend partially through the body 12. As further shown, one or more apertures 30 may also extend along a straight path within the body 12. In other configurations, however, one or more apertures 30 may extend along a curved path. One or more apertures 30 may also intersect within the body 12. Certain implant 10 embodiments may define apertures 30 of different sized configured to provide the above functions Implants 10 may define multiple apertures 30 that extend within the body 12 in the same direction with respect to a body axis X, Y, Z or dimension of the body 12, an example of which is shown in FIG. 3C. These or other implants 10 may further define multiple apertures 30 that extend within the body 12 in different directions with respect to a body axis X, Y, Z, examples of which are shown in FIGS. 3A & 3B. The number, size, and location of apertures 30 may be chosen to promote access of fluids during decalcification and implantation. The apertures 30 may therefore comprise artificially created channels that may cross and intersect each other at various angles to promote access of fluids, both during decalcification and after implantation, to all portions of the body 12 of the graft. In one embodiment, the apertures 30 may be placed as close to each other as possible.

It will be appreciated that implants 10 may comprise apertures 30 extending along any combination of the apertures illustrated in FIGS. 3A-3C. For example, apertures 30 may extend from or between the superior face 14 and the inferior face 15, which may be at parallel, an example of which is shown in FIG. 3C, or at non-parallel angles with respect to the longitudinal axis Z. Apertures 30 may also extend from or between the first lateral face 16 and the second lateral face 17, which may be at parallel, an example of which is shown in FIG. 3A, or at non-parallel angles, an example of which is shown in FIG. 3B, with respect to the lateral axis X. Apertures 30 may also extend from or between the anterior face 19 and the posterior face 18, which may be at parallel, an example of which is shown in FIG. 3A, or non-parallel angles, an example of which is shown in FIG. 3B, with respect to the anterior-posterior axis Y. Apertures 30 may extend from the first lateral face 16 toward or to one of the anterior face 19 and posterior face, an example of which is shown in FIG. 3B. Apertures 30 may also extend from the second lateral face 17 toward or to one of the anterior face 19 and posterior face 18, an example of which is shown in FIG. 3B. Apertures 30 may also extend between the superior face 14 or inferior face 15 and one of the first lateral face 16 or second lateral face 17, the posterior face 18, and the anterior face 19. Apertures 30 may thus extend between a corresponding or opposing face or an adjacent face. In the illustrated embodiments, the apertures 30 are shown stacked with respect to the anterior-posterior axis Y along the first lateral face 16 and second lateral face 17 and stacked with respect to the lateral axis X along the anterior face 19 and the posterior face 18. In other embodiments, apertures 30 may also be stacked along one of the first lateral face 16, second lateral face 17, anterior face 19, or posterior face 18 with respect to the longitudinal axis Z.

In at least one embodiment, an implant 10 comprises a demineralized cortical bone having a flat body 12. A surface of at least one face may include a plurality of grooves 26. The grooves may include any suitable shape or pattern as described above. For example, at least one, such as one or both, of the superior face 16 and the inferior face 17 may include a plurality of gull-wing patterned grooves 26 defined on a surface thereof. Referring again to FIG. 2C, gull-wing patterned grooves 26 may comprise first and second intersecting grooves 26a, 26b. In various embodiments, the body 12 may define gull-wing patterned grooves 26 on both the superior face 14 and inferior face 15, e.g., gull-wing patterned grooves 26 similar to those illustrated in FIG. 2C. In these or other embodiments, the body 12 may include one or more apertures 30 extending between the superior face 14 and inferior face 15 configured to receive osteogenic or other material as described above. To retain osteogenic or other medicinal material the implant 10 can include apertures disposed into the first surface and directed towards the inferior face 15. While in the illustrated embodiment the apertures are disposed entirely through the implant body, it will be appreciated that in other embodiments the apertures may terminate prior to the inferior face 16. Similarly, in some embodiments, apertures 30 may extend from the inferior face 15 toward the superior face 14 but terminate prior to reaching the superior face 14.

In the embodiment illustrated in FIG. 2C, the plurality of grooves 26 are disposed across the superior face 14 and extend between the first lateral face 16 and second lateral face 17, which extend approximately in parallel. In other embodiments, however, the grooves 26 may be oriented in other directions to facilitate different insertion methods. The grooves 26 may be disposed in the superior face 14 or inferior face 15 at any suitable depth, but should not thoroughly alter the biomechanical integrity of the implant. For example, the depth of the grooves into the superior face 14 and inferior face 15 could be approximately 1 mm to approximately 2 mm, and the spacing between the adjacent grooves 26 along the face may be about 1 mm, for example. Moreover, any number of grooves 26 may be included.

Adjacent grooves may extend approximately in parallel as shown in FIGS. 2A-2C. However, in other embodiments, adjacent grooves 26 may extend across a face in other than parallel patterns, such as in increasing or decreasing distances across the face. The grooves 26 shown in FIGS. 2A and 2B extend approximately in parallel between the first lateral face 16 and the second lateral face 17 of the body 12. The ridges formed by the grooves 26 may be used to help maintain an implanted position of the intervertebral implant 10 when sandwiched between adjacent vertebrae by providing and encouraging friction between the ridged surfaces of the implant and vertebrae and thus prevent slipping. Because the grooves 26 and associated ridges extend across the face of the body 12 osteogenic or chondrogenic material which may be placed into the grooves 26 may advantageously be spread across implant-vertebrae interface.

Figure 4:
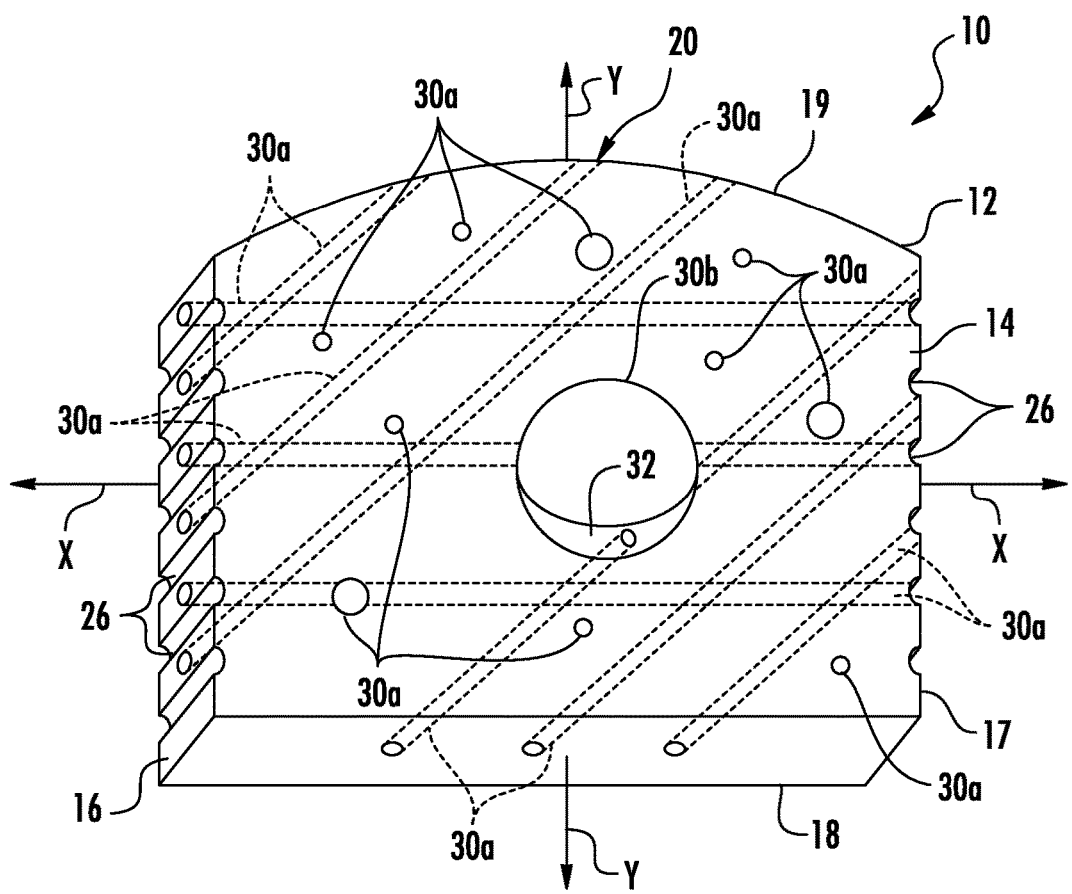
FIG. 4 illustrates an implant body according to various embodiments described herein.

FIG. 4 illustrates an embodiment of an implant 10 wherein the body 12 defines multi-directional and multi-sized apertures 30a, 30b. In some embodiments, for example, the implant 10 defines a plurality of first apertures 30a and one or more second apertures 30b wherein the second apertures 30b have a greater cross-sectional dimension than the first apertures 30a. The first or second apertures 30a, 30b may be configured for attachment of screws, plates, or other fixtures as well as or instead of providing access points for decalcification solution or a reservoir for filler material. The first apertures 30a, having a cross-section or diameter of approximately 1 mm to 2 mm or less may be configured to create a construct which biomechanically mimics cancellous bone structure. The second apertures, having a cross-section greater than 2 mm, such as approximately 3 mm, approximately 4 mm, approximately 5 mm or larger may be configured to accommodate material(s) packed in them. The second apertures 30b may include a central second aperture 30b positioned at a generally central position of the superior face 14 and the inferior face 15 between the first lateral face 16 and second lateral face 17 and have the largest cross-section dimension of the apertures 30a, 30b. The first apertures 30a may extend from one or more of the first lateral face 16 to the second lateral face 17, the anterior face 19 to the posterior face 18, the superior face 14 to the inferior face 15, the anterior face 19 to at least one of the first lateral face 16 and the second lateral face 17, the posterior face 18 to at least one of the first lateral face 16 and the second lateral face 17, and a wall 32 defining a second aperture 30b to one of the first lateral face 16, second lateral face 17, anterior face 19, and posterior face 18. Thus, the first apertures 30a may be multi-directional. The first apertures 30a may also be multi-sized.

As shown, the first apertures 30a extend from the first lateral face 16 to the second lateral face 17, the anterior face 19 to the posterior face 18, the first lateral face 16, and the second lateral face 17, and the superior face 14 to the inferior face 15. The first apertures 30a extend from the superior face 14 to the inferior face 15 substantially parallel to the longitudinal axis Z, the first lateral face 16 to the second lateral face 17 substantially parallel to the lateral axis X, and substantially parallel to the largest dimension of the body 12, e.g., parallel to the vertices formed between the anterior face 19 and the second lateral face 17 and the posterior face 18 and the first lateral face 16. The first apertures 30a are also multi-sized through the superior face 14 and inferior face 15. In another embodiment, first apertures 30a may extend parallel to the corresponding largest dimension between the vertices formed between the anterior face 19 and the second lateral face 17 and the posterior face 18 and the first lateral face 16. The second aperture 30b extends from the superior face 14 to the inferior face 15 substantially parallel to the longitudinal axis Z. In other embodiments, the second aperture 30b or multiple second apertures 30b may extend between different or additional faces.

Still referring to the embodiment illustrated in FIG. 4, the first apertures 30a define cross-sections measuring approximately 2 mm or less, with the larger first apertures 30a shown defining cross-sections approximately 1 mm and the smaller first apertures 30a defining cross-sections less than approximately 0.5 mm or less. The generally centrally positioned second aperture 30b may comprise a cross-section dimension greater than 2 mm such as approximately 3 mm or greater, approximately 5 mm or greater, or approximately 6 mm or greater. In other embodiments, multiple second apertures 30b may be provided wherein at least one second aperture 30b defines cross-section between approximately 2 mm and approximately 3 mm and at least one additional second aperture 30b defines a cross-section greater than 3 mm. The implant 10 body 12 further includes grooves 26 comprising serrations defined along the first lateral face 16 and second lateral face 17 that extend approximately parallel to the longitudinal axis Z.

Additional aperture configurations may be used. For example, in one embodiment, first apertures 30a radiate from the wall 32 defining the second aperture 30b to at least one, including all, of the first lateral face 16, the second lateral face 17, the anterior face 19, and the posterior face 18. In further embodiments, first apertures 30a or second apertures 30b may extend within the body 12 of the implant 10 along paths having other directions or combinations of directions, such as one or more of those described above with respect to FIGS. 3A-3C.

In addition to the dimensions and features described above, implants 10 may incorporate a design comprising one or both of pliability and compressibility. For example, bone material may be harvested from donors and treated such that the resulting altered material, such as altered bone, is pliable and at least partially compressible. In some embodiments, the bone comprises cortical bone or corticocancellous bone. In one embodiment, the bone comprises cancellous bone. According to one method of making an implant 10, the donor bone material may be cut such that the longitudinal length increases anteriorly from the posterior face 18 to the anterior face 19, e.g., as shown in FIGS. 1C & 1D. The treatment is preferably configured to provide compressibility and resilience such that the implant 10 approximates biomechanical properties of an intervertebral disc. The treatment may include partial decalcification or decalcification of the bone material using a decalcification solution. The decalcification solution may include an acid treatment. For example, a suitable decalcification solution may include hydrochloric acid, citric acid, ethylenediaminetetraacetic acid (EDTA), nitric acid, trichloroacetic acid, formic acid, Plank-Rychlo solution, Morse's solution, or a combination thereof. In one embodiment, a chelating decalcifying solution is used comprising EDTA with 0.07% to 10% glycerol or ethylenediaminetetraacetic acid (EDTA)/tris(hydroxymethyl)aminomethane(Tris)-hydrochloride. Decalcification times may vary with different decalcifying solutions. In the present embodiment, decalcification may be performed on bone dehydrated by freeze-drying or hypothermic desiccation. Each decalcifying regiment may be individually controlled by periodic monitoring, e.g., including compression tests, until the desired compressibility is obtained. Decalcification may be enhanced by stirring with a magnetic stirrer, propeller rod, or continuous agitation. Each period in decalcifying solution may be followed by thorough washing in distilled or deionized water. After the bone material is decalcified to a desired level, and washed in distilled water, it may be blotted and desiccated for storage. Alternately the bone may be frozen.

As introduced above, the implant 10 may also comprise accessibility features configured to facilitate decalcification. For example, prior to decalcification treatment, one or more apertures 30 may be drilled, cut, or punched, for example, into the donor bone material at locations configured to facilitate access of the decalcification solution to desired regions of the bone material.

The decalcification process may be monitored to obtain a desired level of decalcification, pliability, and compressibility, e.g., reversible compression, of the bone. The decalcification process may be applied to bone blocks comprising bone material cut into body sizes suitable for spinal implantation or in larger bone block sections that may be subsequently cut into sections corresponding to implant body sizes for spinal implantation. The body 12 may be sized for various intervertebral implantation procedures, e.g., in consideration of the patient, particular location, disc, and outcome desired. For example, the body 12 may be dimensioned such that the longitudinal length increases anteriorly from the posterior face 18 to anterior face 19, as described above. In one embodiment, a longitudinal length of the body 12 taken between the superior face 14 and the inferior face 15 is between approximately 0.2 cm and approximately 3 cm, 1.5 cm to 3.0 cm, or in one embodiment, 1.5 cm to 5 cm. In a lordotic configuration, for example, when the longitudinal length of the body 12 increases anteriorly, the difference between the longitudinal length of the body 12 adjacent to the anterior face 19 and the longitudinal length of the body 12 adjacent to the posterior face 18 may be approximately 2 mm to approximately 3 mm. This body 12 may be pliable and reversibly compressible along the longitudinal dimension, such as by at least approximately 20% upon compression. The anterior-posterior dimension of the body 12 taken along the first lateral face 16 and the second lateral face 17 between the anterior face 19 and posterior face 18 may be between approximately 1 cm and approximately 3 cm.

As described above, the body 12 may also be prepared such that the anterior face 19 extends along a convex curve between the first lateral face 16 and the second lateral face 17. Accordingly, in such embodiments, the length of the anterior-posterior dimension taken along the first lateral face 16 and the second lateral face 17 between the anterior face 19 and posterior face 18 is less than the length of the greatest anterior-posterior dimension of the body taken between the anterior face 19 and posterior face 18 along the superior face 14 or inferior face 15. The anterior-posterior dimension between the posterior face 18 and the curve 32 may be between approximately 1.5 cm and approximately 5.0. In lordotic configurations, the lateral dimensions of the body 12 may conform to the anterior-posterior slope. In one embodiment, the lateral dimensions conform to approximately a 10° to 15° slope. In one embodiment, the average anterior-posterior length between the anterior face 19 and the posterior face 18 taken along the superior face 14 or inferior face 15 is approximately 1.5 cm. The anterior-posterior length of the body 12 taken between the anterior face 19 and the posterior face 18 is preferably reversibly compressible between 40% to 60% of the uncompressed size. In one embodiment, the anterior-posterior length taken between the anterior face 19 and the posterior face 18 may be reversibly compressible by approximately 60%. The compression may be measured across the entire anterior-posterior dimension. In generally achieving desired compression includes consideration of the original density of the bone and the degree of decalcification.

Following decalcification, including partial decalcification, the body 12 may be dehydrated to obtain a dehydrated form. In such embodiments, the body 12 is rehydratable to obtain a hydrated form. In addition to or alternatively, the bone material may be preserved by freezing, cryopreservation, freeze-drying, hypothermic dehydration or chemical dehydration, for example. Upon dehydration, the body 12 may decrease in size, e.g., in volume or in one or more dimensions, compared to the hydrated form. Upon rehydration the implant 10 may transition to the hydrated form thereby increasing in size, e.g., in volume or in one or more dimensions. For example, in one embodiment, the body 12 increases in volume almost two fold in the hydrated form compared to the dehydrated form. In one embodiment, a dimension of the body 12 increases almost two fold or more in the hydrated form compared to the dehydrated form. In some configurations, one body dimension stays approximately the same and another body dimension increases approximately less than two fold, approximately two fold, approximately three fold, or between almost two fold and approximately three fold. For example, a lateral length of the body 12 may be approximately the same in both the dehydrated and hydrated forms and an anterior-posterior dimension may increase approximately less than two fold, approximately two fold, approximately three fold, or between almost two fold and approximately three fold from the dehydrated form to the hydrated form. In one configuration, for example, a lateral length of the body 12 taken between the first lateral face 16 and the second lateral face 17 is approximately the same in both the dehydrated form and the hydrated form, but the smallest anterior-posterior dimension in the dehydrated form may be approximately 0.5 cm compared to approximately 1.5 cm in the hydrated form.

Figure 5A:
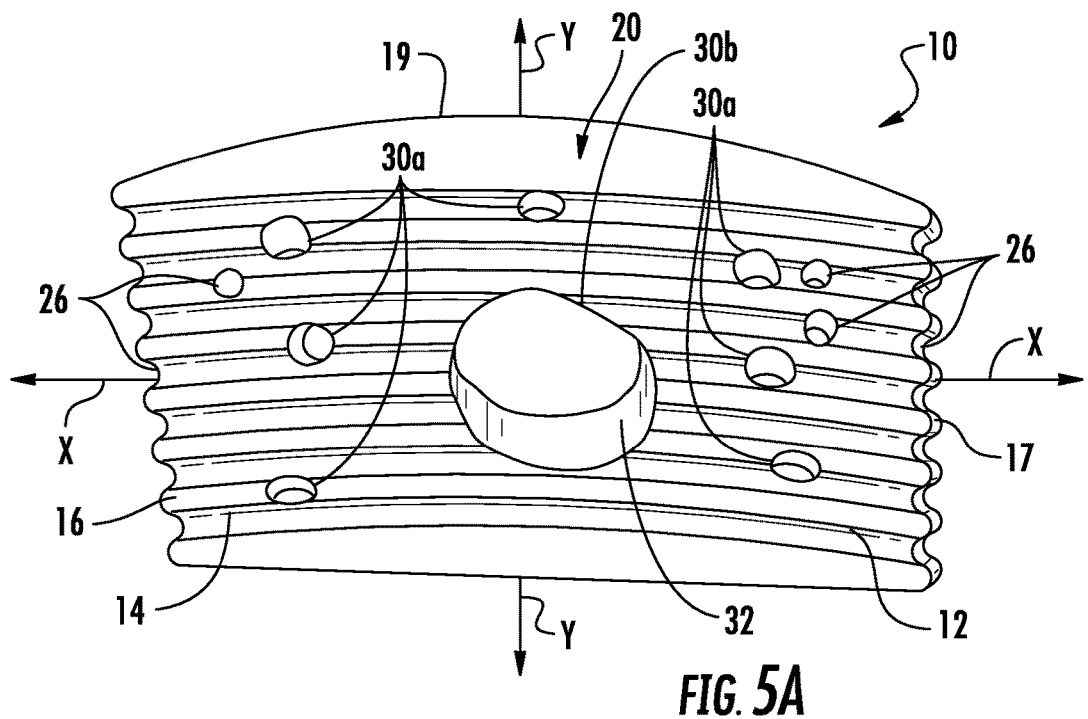
FIGS. 5A & 5B illustrate a decalcified cortical implant in a dehydrated form according to various embodiments described herein.
Figure 5B:
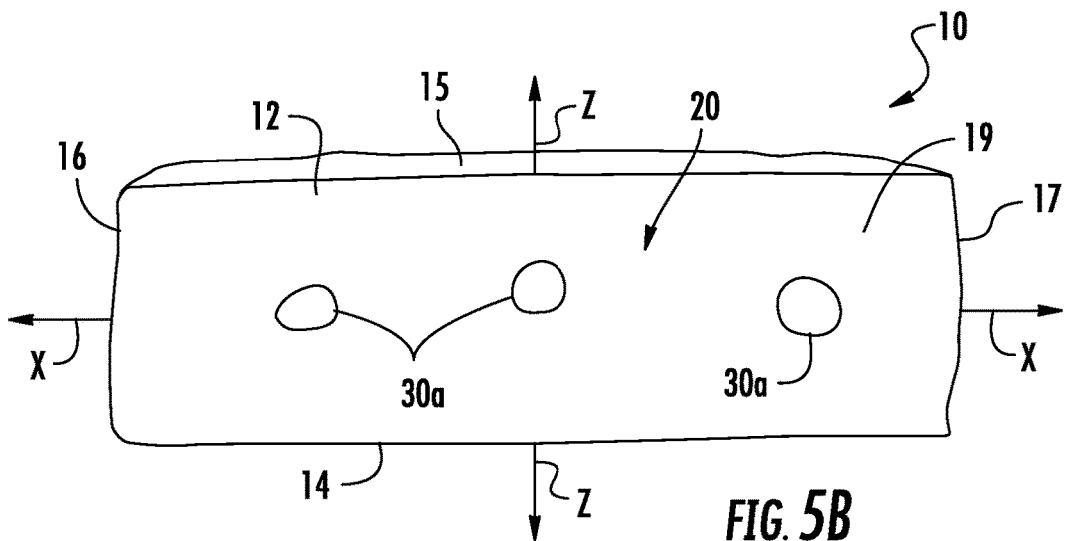

FIGS. 5A & 5B are photographic depictions, including scale (markings correspond to 0.5 cm), of a body 12 of an implant 10 in a dehydrated form, e.g., after being subjected to dehydration, according to one embodiment. The body 12 may comprise a body plan similar to that described above with respect to the body plans illustrated in any one of FIGS. 1A-1D and the accompanying discussion. The body 12 shown is formed of cortical bone, but other types of bone described above may be used, such as cancellous or corticocancellous bone.

A plurality of apertures 30a, 30b extend through the body 12. In further embodiments, the apertures 30a, 30b may extend through the body 12 in any combination as described above, for example as described with respect to FIG. 4. The apertures 30a, 30b comprise a plurality of multi-directional first apertures 30a and a second aperture 30b. The second aperture 30b extends from the superior face 14 to the inferior face 15 (not visible in FIG. 5A) approximately parallel to the longitudinal axis Z. In one embodiment, the second aperture 30b is dimensioned to receive nucleus pulposus material. The second aperture 30b is located at a generally central position of the superior face 14 and inferior face 15 (not visible) with respect to the first lateral face 16 and second lateral face 17. FIG. 5B shows a plurality of first apertures 30a extending from the anterior face 19 to the posterior face 18 (not visible) substantially parallel to the anterior-posterior axis Y. The centrally positioned first aperture 30a along the anterior face 19 extends from the anterior face 19 to a wall 32 of the second aperture 30b and from a diametrically opposed portion of the wall 32 to the posterior face 18. The first apertures 30a have a cross-section dimension of approximately 2 mm or less. The second aperture 30b has lateral to lateral and anterior-posterior cross-section dimensions of approximately 0.38 cm. The lateral to lateral length of the body 12 taken between the first lateral face 16 and the second lateral face 17 is approximately 1.5 cm.

The body 12 further includes a plurality of grooves 26 formed along the superior face 14. In one embodiment, the inferior face 15 (not visible) may also include grooves 26. The grooves 26 extend lateral to lateral across the superior face 14 along a slight anteriorly directed curve between the first lateral side 16 and the second lateral side 17. The grooves 26 extending along the superior face 14 comprise gull-wing patterned grooves 26. Grooves 26 are also formed along the first lateral face 16 and the second lateral face 17 and extend approximately parallel to the longitudinal axis Z. The grooves 26 along the first lateral face 16 and second lateral face 17 comprise serrations and approximately align with the gull-wing patterned grooves 26 extending along the adjacent surfaces of the superior face 14.

Still referring to the embodiment shown in FIGS. 5A & 5B, the length of the anterior-posterior dimension is approximately 0.75 cm at the lateral edges and increases to approximately 0.88 cm therebetween. The superior face 14 and the inferior face 15 extend approximately parallel, and the length of the longitudinal dimension taken between the superior face 14 and the inferior face 15 along the anterior face 19 is approximately 0.5 cm.

Figure 6A:
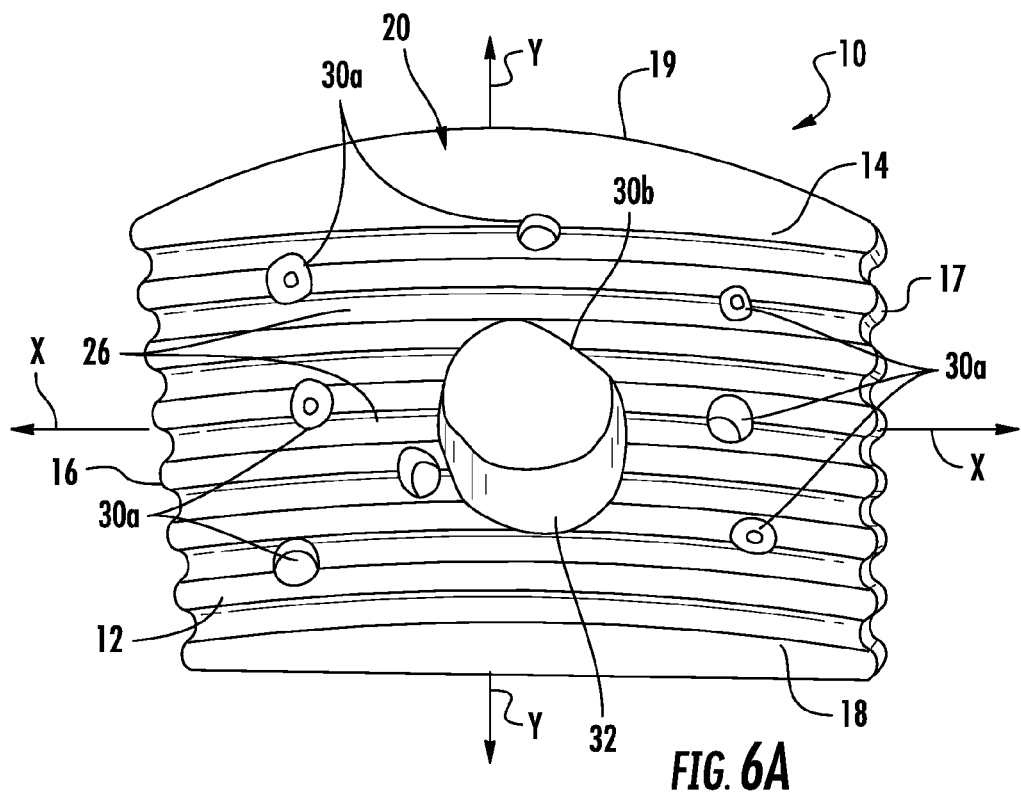
FIGS. 6A & 6B illustrate the decalcified cortical implant of FIGS. 5A & 5B in a hydrated form according to various embodiments described herein.
Figure 6B:
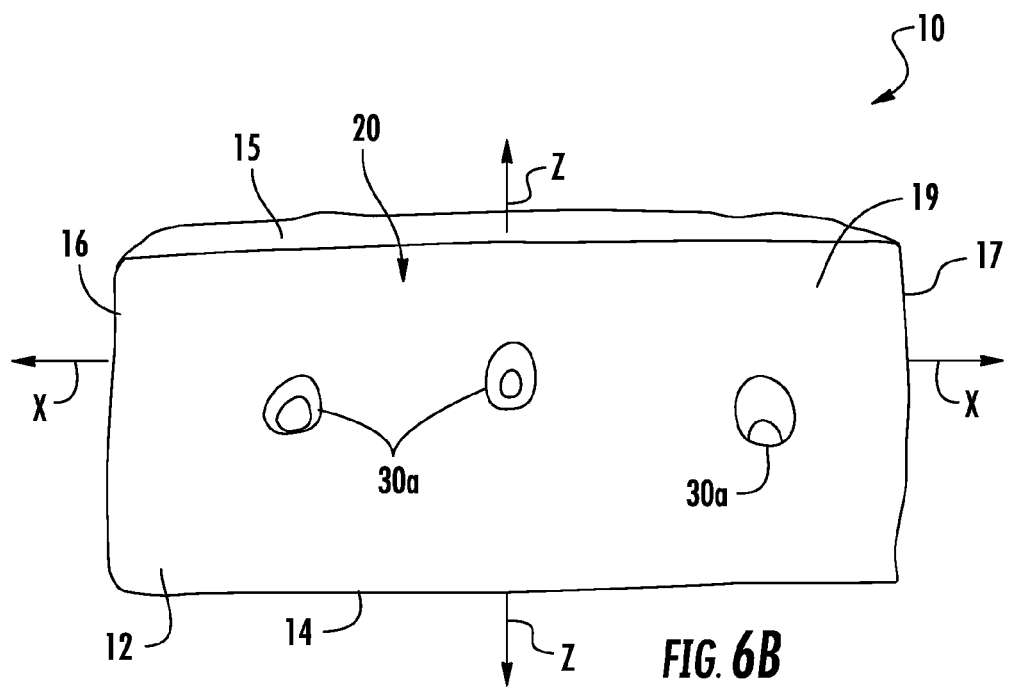
Figure 6C:
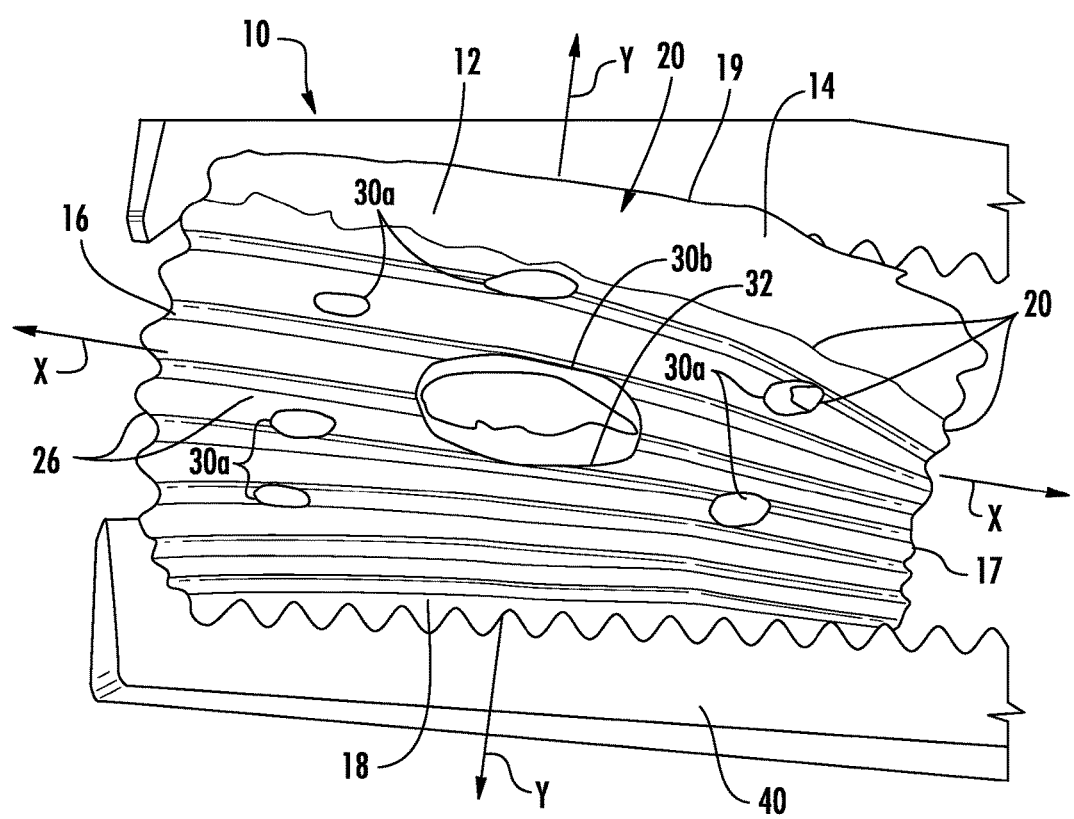
FIG. 6C illustrates the decalcified cortical implant of FIGS. 5A-6B in a hydrated form being reversibly compressed with a Kocher clamp according to various embodiments described herein.

FIGS. 6A-6C are photographic depictions including scale (markings correspond to 0.5 cm) of the body 12 shown in FIGS. 5A & 5B in a hydrated form. In this embodiment, the lateral to lateral dimensions of the body 12 are relatively constant between the hydrated and dehydrated forms; however, the anterior to posterior and longitudinal dimensions increase at least 20% from the dehydrated form to the hydrated form, with a greater percentage increase obtained in the longitudinal dimension. In the hydrated form, the first apertures 30a have cross-sections of approximately 2 mm or less. The second aperture 30b has lateral to lateral cross-section of approximately 0.38 cm and an anterior-posterior cross-sections of approximately 0.45 cm. The lateral to lateral length of the body 12 taken between the first lateral face 16 and the second lateral face 17 is approximately 1.5 cm. The length of the anterior-posterior dimension is approximately 0.95 cm at the lateral edges and increases to approximately 1.10 cm therebetween. The length of the longitudinal dimension taken between the superior face 14 and the inferior face 15 is approximately 0.75 cm. FIG. 6C illustrates partial compression of the body 12 by approximately 20% with a Kocher clamp 40 along the anterior-posterior dimension. Upon removal of compression, the body 12 will return to the uncompressed hydrated dimensions.

In various embodiments, the implant 10 may comprise one or more structures configured to promote disc regeneration. For example, the implant 10 may comprise structural features such as apertures 30 or grooves 26, as described above, dimensioned to interact with native tissues or in situ environment upon implantation to promote disc regeneration, via one or more properties providing osteoconduction, osteoinduction, or osteogenisis of the implant 10. As a further example, the structural features may provide locations for disc regeneration or reservoirs for carrying disc regeneration materials. The above described apertures 30 or grooves 26 formed in the implant body 12, for example, may serve as vehicles or carriers of disc regeneration materials. Disc regeneration materials may include cellular material such as stem cells, e.g., pluripotent stem cells, bone marrow, or cells derived from bone marrow. Disc regeneration materials may also include micronized or microparticulate materials, examples of which may comprise one or more of micronized vertebral body end plates, nucleus pulposus, microparticulate nucleus pulposus, micoparticulate cartilage which may include cartilage obtained from the end-plates of the vertebrae, or microparticulate bone preparations, including bone from peristeum or endosteum.

In one embodiment, one or more apertures 30 or grooves 26 may be filled with an osteogenic material. In this or another embodiment, one or more apertures 30 or grooves 26 may be filled with a condrogenic material. In one of these embodiments or another embodiment, one or more apertures 30 or grooves 26 may be filled with material from the nucleus pulposus. In various embodiments, the above materials may comprise non-demineralized tissue, demineralized tissue, demineralized bone, cartilage or nucleus pulposus, partially demineralized materials, autolyzed, antigen-extracted, allogeneic (AAA) bone, or osteogenic bone factors including bone morphogenic proteins (BMP's). In one embodiment, the implant 10 comprises apertures 30 filled with osteogenic material, condrogenic material, or material from the nucleus pulposus consisting of one or more of non-demineralized tissue, demineralized tissue, demineralized bone, cartilage or nucleus pulposus, partially demineralized materials, autolyzed, antigen-extracted, allogeneic (AAA) bone, or osteogenic bone factors including bone morphogenic proteins (BMP's).

While various illustrated embodiments are shown having faces generally intersecting at points or generally straight angled edges, it is to be understood that such edges may be arcuate or rounded. For example, in some embodiments, the superior face 14 may intersect with the first lateral face 16, the second lateral face 17, the posterior face 17, the anterior face 19, or any combination thereof along curved edges, e.g., rounded or arcuate. In these or other embodiments, the inferior face 15 may intersect with the first lateral face 16, the second lateral face 17, the posterior face 17, the anterior face 19, or any combination thereof along curved edges, e.g., rounded or arcuate. In these of other embodiments, one or more edges or portions of the edges along the interfacing portions of the posterior face 18 and the first lateral face 16, the first lateral face 16 and the anterior face 19, the anterior face 19 and the second lateral face 17, and the second lateral face 17 and the posterior face 18 may be curved, e.g., rounded or arcuate. Thus, in some embodiments, the first lateral face 16, second lateral face 17, posterior face 18, and anterior face 19 may together define a general "D" shape, wherein one or more of the edges may be curved. In one embodiment, the first lateral face 16, second lateral face 17, posterior face 18, and anterior face 19 intersect along curved edges. In one such embodiment, the first lateral face 16, second lateral face 17, posterior face 18, and anterior face 19 may together define a regular or irregular arcuate, oval, circular, or general "O" shape. In one further embodiment, the body 12 defines a cylinder. The implant 10 may be provided in a variety of shapes to suit a particular application.

While the above description is generally provided with reference to implants for spinal implantation and related procedures, the teachings herein may be used to provide implants for other bone implantation procedures. For example, the implant may be provided in a variety of shapes, e.g., having regular or irregular cross-sections or forming geometric or non-geometric shapes, to suit a particular application. Such an implant may be prepared as described above and may thus be configured with surface grooves, apertures, or combinations of surface grooves and apertures as herein described. In one embodiment, the implant may be prepared in varieties of shapes, e.g., a cylinder, for application in vertical or horizontal mandibular or maxillary ridge augmentation. In one such embodiment, the implant may include includes grooves formed along the circumferential surface corresponding to the lateral, posterior, and anterior faces. In this or another embodiment, the implant may include apertures extending into or through the body.

In various embodiments, the implant 10 may comprise a non-osteogenic implant 10 having a body 12 configured to separate the adjacent vertebrae and configured as a vehicle to carry or deliver substances such as filler materials to promote disc regeneration. Promoting disc regeneration may include initiating, enhancing, directing, localizing, or driving disc regeneration, for example. The non-osteogenic implant 10 may be prepared as described above and therefore be formed of decalcified or partially decalcified cortical or cancellous bone having the dimensions, pliability, and compressibility as described above. However, the implant 10 may be rendered inert, e.g., using one or more chemical or physical methods. For example, the implant 10 may be rendered inert by exposure to hydrogen peroxide, irradiation, or another physical or chemical methodology known in the art. These inert non-osteogenic implants 10 may serve as vehicles or carriers of disc regeneration filler materials such as micronized vertebral body end plates, nucleus pulposus, or pluripotent stem cells, for example. Accordingly, the present disclosure may comprise an intervertebral spine implant 10 including a postreolateral or other extradisk space implant 10 made of readily available altered cortical bone. In one embodiment, the bone forming the implant body 12 may be altered with respect to a bone regeneration property. For example, the body 12 may be chemically treated with hydrogen peroxide, or treated with ionizing radiation to substantially reduce or abolish osteogenic potential. Treatment with ionizing radiation may include doses of from about 20 to about 60 Gray, for example. Implants 10 so treated to substantially reduce or abolish osteogenic potential may also include apertures 30 or grooves 26, as described above, forming material reservoirs. In one embodiment, a non-osteogenic implant 10 prepared as above may be configured to serves substantially exclusively as a vehicle to deliver growth promoting materials located or lodged in its apertures 30 or grooves 26. In another embodiment, the implant 10 may comprise a body 12 configured to serve as a vehicle or carrier of one or more osteoinductive substances and at the same time provide support to the vertebral column.

In various embodiments, a method of implanting the intervertebral implant 10 may comprise implanting the implant 10 as an intervertebral disc replacement. In one embodiment, a method of treating flat back deformity or loss of lordosis comprises intervertebral implantation of the intervertebral implant 10 as described above.

In further embodiments, implants prepared in a manner similar to that described above with respect to the intervertebral implants 10 may comprise long onlay or inlay grafts for vertebral implantation. For example, the implant 10 may comprise a flat plate or plate like graft configured for use as an inerspinous or inertransverse process graft prepared as described above with respect to the intervertebral implant 10. In some embodiments, screws, plates, or other fixtures may be utilized to maintain alignment of the spinal column during recovery of the intervertebral disc or the fusion of the vertebrae. During a procedure, implants 10 may be mechanically joined together by a keystone type device or similar anchoring device to increase the size of the implant 10. In these or other embodiments, it may be desirable to incorporate osteogenic material with intervertebral or intertransverse or other inlay or onlay grafts.

This specification has been written with reference to various non-limiting and non-exhaustive embodiments. However, it will be recognized by persons having ordinary skill in the art that various substitutions, modifications, or combinations of any of the disclosed embodiments (or portions thereof) may be made within the scope of this specification. Thus, it is contemplated and understood that this specification supports additional embodiments not expressly set forth in this specification. Such embodiments may be obtained, for example, by combining, modifying, or reorganizing any of the disclosed steps, components, elements, features, aspects, characteristics, limitations, and the like, of the various non-limiting and non-exhaustive embodiments described in this specification. In this manner, Applicant reserves the right to amend the claims during prosecution to add features as variously described in this specification, and such amendments comply with the requirements of 35 U.S.C. §§112(a) and 132(a).

What is claimed is:

1. An allogeneic or xenogeneic implant for intervertebral disc replacement, the implant comprising
    a body formed of partially decalcified cortical bone, the body extending along a longitudinal axis between a superior face and an inferior face, a lateral axis between a first lateral face and a second lateral face, and an anterior-posterior axis between an anterior face and a posterior face;
    a plurality of tubular apertures defined within the body, the plurality of apertures positioned to allow inflow of decalcifying solutions for rapid and uniform decalcification, wherein, after partial decalcification, the body is pliable and compressible;
    wherein the plurality of apertures include a first set of apertures that each extend from the superior face to the inferior face, each of the first set of apertures having a cross-section greater than 2 mm;
    wherein the plurality of apertures include a second set of apertures, each of the second set of apertures having a cross-section of 2 mm or less, the second set of apertures including:
        a first aperture that extends from the first lateral face to the second lateral face at an angle that is not parallel to the lateral axis;
        a second aperture that extends from the anterior face to the posterior face at an angle that is not parallel to the anterior-posterior axis; and
        a third aperture that extends from the first lateral face to the second lateral face at an angle that is not parallel to the lateral axis, the third aperture intersecting with a fourth aperture that extends from the anterior face to the posterior face at an angle that is not parallel to the anterior-posterior axis.

2. The implant of claim 1, wherein one or more of the first set of apertures are filled with at least one filler material selected from an osteogenic material, a chondrogenic material, or a nucleus pulposus material.

3. The implant of claim 2, wherein the filler material further comprises at least one material selected from the group consisting of non-demineralized tissue, demineralized tissue, demineralized bone, cartilage or nucleus pulposus, partially demineralized materials, autolyzed antigen-extracted allogeneic bone, and osteogenic bone factors including bone morphogenetic proteins.

4. The implant of claim 1, wherein the partially decalcified bone is prepared from bone material, with at least one bone material selected from cortical bone or corticocancellous bone.

5. The implant of claim 4, wherein the bone material is obtained from at least one source selected from a femur, tibia, humerus, ilium, or vertebral body.

6. The implant of claim 4, wherein the anterior face extends at a convex angle between the first and second lateral faces.

7. The implant of claim 6, wherein a longitudinal thickness of the body between the superior face and the inferior face increases anteriorly from the posterior face configured to produce a lordotic configuration of a spine of a patient.

8. The implant of claim 7, wherein the superior face and the inferior face are inclined with respect to each other anteriorly from the posterior face.

9. The implant of claim 7, wherein the superior face and inferior face extend anteriorly from the posterior face at a combined angle greater than 180°.

10. The implant of claim 6, wherein the superior face and the inferior face together extend between the posterior face and anterior face approximately parallel.

11. The implant of claim 6, wherein the body comprises an anterior-posterior length extending between the anterior face and the posterior face, and wherein the anterior-posterior length along the first lateral face and the second lateral face is between approximately 1 cm and approximately 3 cm.

12. The implant of claim 6, wherein an average anterior-posterior length between the anterior face and the posterior face is approximately 1.5 cm to approximately 3.5 cm.

13. The implant of claim 6, wherein the body is dehydratable to obtain a dehydrated form and rehydratable to obtain a hydrated form.

14. The implant of claim 13, wherein a dimension of the body increases two-fold from the dehydrated form to the hydrated form.

15. The implant of claim 13, wherein a longitudinal length of the body in the hydrated form taken between the superior face and the inferior face in the hydrated form is between approximately 0.2 cm and approximately 3 cm and is reducible by approximately 20% upon compression.

16. The implant of claim 13, wherein an anterior-posterior length of the body taken between the anterior face and the posterior face is reversibly compressible by approximately 40% to approximately 60% in the hydrated form.

17. The implant of claim 13, wherein a lateral length of the body taken between the first lateral face and the second lateral face is approximately the same in both the dehydrated form and the hydrated form, and wherein the smallest anterior-posterior dimension in the dehydrated is approximately 0.5 cm and approximately 1.5 cm in the hydrated form.

18. The implant of claim 6, further comprising a plurality of grooves defined along a surface of at least one face selected from the superior face, inferior face, first lateral face, or second lateral face.

19. The implant of claim 18, wherein the grooves comprise ridges that extend across at least one of the superior face or the inferior face.

20. The implant of claim 18, wherein the grooves comprise gull-wing patterned grooves that extend across at least one of the superior face or the inferior face.

21. The implant of claim 20, wherein the grooves comprise serrations, wherein the serrations extend across at least one of the first lateral face or the second lateral face.

22. The implant of claim 6, wherein an average anterior-posterior length of the body is approximately 1.5 cm, and wherein the grooves comprise serrations that extend across the first lateral face and the second lateral face.

23. The implant of claim 6, wherein the implant is one of frozen, cryopreserved, freeze-dried, hypothermically dehydrated, and chemically dehydrated.

24. An intervertebral implant comprising:
a body formed of partially decalcified cortical bone, the body extending along a longitudinal axis between a superior face and an inferior face, a lateral axis between a first lateral face and a second lateral face, and an anterior-posterior axis between an anterior face and a posterior face, wherein the first lateral face, second lateral face, anterior face, and posterior face together define a general "D" shape, wherein the first lateral face and second lateral face extend generally straight with respect to the anterior-posterior axis and generally in parallel, wherein the posterior face extends generally straight with respect to the lateral axis, and wherein the anterior face is generally curves away from the posterior face between the first lateral face and second lateral face;
a plurality of gull-wing patterned grooves formed on at least one of the superior face and the inferior face;
an osteogenic material received within at least one of the grooves; and
a plurality of tubular apertures defined within the body, the plurality of apertures positioned to allow inflow of decalcifying solution for rapid and uniform decalcification, wherein, after partial decalcification, the body is pliable and compressible, wherein the plurality of apertures comprise:
a first set of apertures defined within the body and extending from the superior face to the inferior face, each of the first set of apertures having a cross-section greater than 2 mm; and
a second set of apertures having a cross-section of 2 mm or less, the second set of apertures including
a first aperture defined within the body and extending from the first lateral face to the second lateral face at an angle that is not parallel to the lateral axis;
a second aperture defined within the body and extending from the anterior face to the posterior face at an angle that is not parallel to the anterior-posterior axis; and
a third aperture defined within the body and extending from the first lateral face to the second lateral face at an angle that is not parallel to the lateral axis, the third aperture intersecting with a fourth aperture defined within the body and extending from the anterior face to the posterior face at an angle that is not parallel to the anterior-posterior axis.

25. The implant of claim 24, wherein the bone material is obtained from a femur.

26. The implant of claim 24, wherein the osteogenic potential of the bone has been abolished by hydrogen peroxide treatment.

27. The implant of claim 24, wherein the osteogenic potential of the bone has been abolished by ionizing radiation treatment in doses ranging from approximately 20 Gray to approximately 60 Gray.

28. The implant of claim 24, wherein a microparticulate material is received in one or more of the grooves, one or more of the plurality of apertures, or a combination thereof, wherein the microparticulate material comprises at least one material selected from microparticulate nucleus pulposus, microparticulate cartilage comprising cartilage obtained from vertebrae end-plates, or microparticulate bone preparations comprising bone from periosteum and endosteum.

29. The implant of claim 24, wherein bone marrow, cells derived from bone marrow, or a combination thereof are positioned in one or more of the grooves, one or more of the plurality of apertures, or a combination thereof.

\* \* \* \* \*